(12) United States Patent
Mullen et al.

(10) Patent No.: US 10,137,091 B2
(45) Date of Patent: Nov. 27, 2018

(54) IMMEDIATE/DELAYED DRUG DELIVERY

(75) Inventors: Alexander Mullen, Glasgow (GB);
Howard Stevens, Glasgow (GB);
Sarah Eccleston, Glasgow (GB)

(73) Assignee: UNIVERSITY OF STRATHCLYDE, Glasgow (GB)

( * ) Notice: Subject to any disclaimer, the term of this patent is extended or adjusted under 35 U.S.C. 154(b) by 976 days.

(21) Appl. No.: 13/582,940

(22) PCT Filed: Mar. 4, 2011

(86) PCT No.: PCT/GB2011/000314
§ 371 (c)(1),
(2), (4) Date: Oct. 2, 2012

(87) PCT Pub. No.: WO2011/107755
PCT Pub. Date: Sep. 9, 2011

(65) Prior Publication Data
US 2013/0017262 A1 Jan. 17, 2013

(30) Foreign Application Priority Data
Mar. 5, 2010 (GB) .................................. 1003731.5

(51) Int. Cl.
A61K 9/42 (2006.01)
A61K 9/20 (2006.01)
A61K 9/24 (2006.01)
A61K 31/00 (2006.01)
A61K 31/196 (2006.01)
A61K 38/00 (2006.01)

(52) U.S. Cl.
CPC ............ A61K 9/2054 (2013.01); A61K 9/209 (2013.01); A61K 9/2018 (2013.01); A61K 9/2068 (2013.01); A61K 31/00 (2013.01); A61K 31/196 (2013.01); A61K 38/00 (2013.01)

(58) Field of Classification Search
None
See application file for complete search history.

(56) References Cited

U.S. PATENT DOCUMENTS

| | | | |
|---|---|---|---|
| 4,832,958 A | 5/1989 | Baudier et al. | |
| 4,871,549 A * | 10/1989 | Ueda et al. | 424/494 |
| 5,145,644 A | 9/1992 | Park et al. | |
| 5,508,044 A * | 4/1996 | Buxton et al. | 424/495 |
| 5,558,879 A * | 9/1996 | Chen et al. | 424/480 |
| 5,614,220 A | 3/1997 | Hirakawa et al. | |
| 5,788,987 A | 8/1998 | Busetti et al. | |
| 6,312,724 B1 | 11/2001 | Odidi et al. | |
| 6,610,323 B1 | 8/2003 | Lundberg et al. | |
| 6,632,451 B2 * | 10/2003 | Penhasi et al. | 424/464 |
| 6,740,339 B1 | 5/2004 | Ohkouchi et al. | |
| 8,168,218 B2 * | 5/2012 | Vergnault et al. | 424/464 |
| 2004/0062804 A1 | 4/2004 | Lee et al. | |
| 2004/0241100 A1 | 12/2004 | Kramer et al. | |
| 2005/0152974 A1 | 7/2005 | Boehm et al. | |
| 2005/0220877 A1 | 10/2005 | Patel et al. | |
| 2006/0177506 A1 | 8/2006 | Yanai et al. | |
| 2006/0257482 A1 | 11/2006 | Kumar et al. | |
| 2007/0098788 A1 | 5/2007 | Gore et al. | |
| 2009/0053308 A1 | 2/2009 | Ishida et al. | |
| 2009/0155358 A1 | 6/2009 | Diaz et al. | |
| 2009/0297601 A1 | 12/2009 | Vergnault et al. | |
| 2010/0040557 A1 | 2/2010 | Ke et al. | |
| 2013/0022676 A1 | 1/2013 | Mullen et al. | |
| 2013/0022677 A1 | 1/2013 | Mullen et al. | |

FOREIGN PATENT DOCUMENTS

| | | |
|---|---|---|
| EP | 0 546 593 A1 | 6/1993 |
| EP | 1 064 937 | 1/2001 |
| EP | 1 607 092 A1 | 12/2005 |
| EP | 2 098 250 A1 | 9/2009 |
| JP | H05-194188 A | 8/1993 |
| JP | 2001-515854 A | 9/2001 |
| JP | 2001-322927 A | 11/2001 |
| JP | 2003-503340 A | 1/2003 |
| JP | 2004-300148 A | 10/2004 |
| JP | 2005-508326 A | 3/2005 |
| JP | 2005-508327 A | 3/2005 |
| JP | 2005-508328 A | 3/2005 |
| JP | 2005-510477 A | 4/2005 |
| JP | 2008-517970 A | 5/2008 |
| JP | 2009-514989 A | 4/2009 |
| WO | WO 99/12524 A1 | 3/1999 |
| WO | WO 01/00181 A2 | 1/2001 |

(Continued)

OTHER PUBLICATIONS

Ghimire et al. (European Journal of Pharmaceutics and Biopharmaceutics 67, 515-523, 2007.*
Stevens, H.N.E., "Chronopharmaceutical Drug Delivery," Journal of Pharmacy and Pharmacology, 1998, 50 (Supplement 9), 5.
International Search Report and Written Opinion of the International Searching Authority for International Application No. PCT/GB2011/000306, dated Mar. 12, 2012, 15 pages.
International Search Report and Written Opinion of the International Searching Authority for International Application No. PCT/GB2011/000307, dated Mar. 12, 2012, 14 pages.

(Continued)

*Primary Examiner* — Tigabu Kassa
(74) *Attorney, Agent, or Firm* — Hoxie & Associates LLC

(57) ABSTRACT

In one aspect, the present invention is concerned with a treatment where it is desired that an active agent is designed to be released immediately following administration and again at a time point some time after administration of the active agent. The present invention is particularly suited to administering an agent which may be released before sleep and while a subject is sleeping. As well as treating certain conditions by a particular regime, the invention also provides novel formulations for an immediate, followed by a delayed release of drug.

13 Claims, 4 Drawing Sheets

(56) References Cited

FOREIGN PATENT DOCUMENTS

| WO | WO 03/026615 A2 | | 4/2003 |
|----|----|----|----|
| WO | WO 03/026625 A1 | | 4/2003 |
| WO | WO 03/026626 A2 | | 4/2003 |
| WO | WO 03/030920 A1 | | 4/2003 |
| WO | WO 2006/045618 A1 | | 5/2006 |
| WO | WO 2008/079102 A1 | | 7/2008 |
| WO | WO 2008/081891 A1 | | 7/2008 |
| WO | WO 2008/129517 | * | 10/2008 |
| WO | WO 2009/154810 A2 | | 12/2009 |

OTHER PUBLICATIONS

Ghimire, M. et al. "In-vitro/In-vivo Correlation of Pulsatile Drug Release from Press-Coated Tablet Formulations: A Pharmacoscintigraphic Study in the Beagle Dog," European Journal of Pharmaceutics and Biopharmaceutics, 2007, vol. 67, No. 2, 515-523.
Written Opinion of the International Searching Authority (Form PCT/ISA/237) dated Mar. 12, 2012, for International Application No. PCT/GB2011/000314, 14 pages.
Alvarez-Lorenzo, C. et al., "Evaluation of Low-substituted Hydroxypropylcelluloses (L-HPCs) as Filler-Binders for Direct Compression," International Journal of Pharmaceutics, 2000, 197, 107-116.
English-language abstract of JP 2001-322927, Date of publication of application Nov. 20, 2001, 1 page.
English-language machine translation of JP 2001-322927, retrieved from the Japanese Patent Office website on May 2, 2015, 15 pages.
Fukui, E. et al., "Studies on Applicability of Press-coated Tablets Using Hydroxypropylcellulose (HPC) in the Outer Shell for Timed-release Preparations," Journal of Controlled Release, 2000, 68, 215-223.
Rowe, R. et al., Eds., Handbook of Pharmaceutical Excipients, Sixth Edition, Pharmaceutical Press, London, 2009, pp. 317-324.
Shin-Etsu Guide on Low Substituted Hydroxypropyl Cellulose NF, U.S. Appl. No. 13/582,913 in which Examiner listed publication date as 2008.
Kleinebudde, P., "Application of Low Substituted Hydroxypropycellulose (L-HPC) in the Production of Pellets Using Extrusion / Spheronization" International Journal of Pharmaceutics, 96, pp. 119-128, (1993).
Shin-Etsu, Pharmaceutical Excipients, Guide to Application, Table, 1 page (2015).
Shin-Etsu, Low-Substituted Hydroxypropyl Cellulose NF (L-HPC), 23 pages (2015).

* cited by examiner

IMMEDIATE/DELAYED DRUG DELIVERY

CROSS REFERENCE TO RELATED APPLICATIONS

This application is a United States Application under 35 U.S.C. 371 claiming benefit of PCT Application No. PCT/GB2011/000314, filed on Mar. 4, 2011, which claims the benefit of GB 1003731.5, filed on Mar. 5, 2010, the contents of each of which are incorporated herein by reference.

FIELD OF INVENTION

In one aspect, the present invention is concerned with a treatment where it is desired that an active agent is designed to be released immediately following administration and again at a time point some time after administration of the active agent. The present invention is particularly suited to administering an agent which may be released before sleep and whilst a subject is sleeping. As well as treating certain conditions by a particular regime, the invention also provides novel formulations for an immediate, followed by a delayed release of drug.

BACKGROUND TO THE INVENTION

Time-dependent release mechanisms of drugs have been described in the literature for tablet, pellet and capsule formulation utilising a wide range of physicochemical and physicomechanical strategies. The common feature of all such formulations is that they are activated by contact with fluids following ingestion by the patient and the drug will be released at the predetermined time after administration. Only after the formulations come into contact with gastric fluids does the 'clock' start.

Drug release subsequently takes place at a predicted time, although it will be appreciated that since the dosage unit will be travelling through the GI tract during the lag period, drug release will necessarily be at some unknown GI tract site. Using such formulation strategies, it will be possible to design delivery systems capable of releasing drugs according to chronotherapeutic principles and targeting release to the circadian rhythm of disease states (Stevens H N E, *Chronopharmaceutical Drug Delivery. J Pharm Pharmac,* 50 (s) 5 (1998))

However, many of the formulations in the art rely on complex structures which can add to the cost of the manufacture of the drug and/or can be subject to malfunction leading to incorrect/inappropriate administration of the drug.

Diclofenac is a non-steroidal anti-inflammatory drug (NSAID) which is taken to reduce inflammation and as an analgesic reducing pain in conditions such as arthritis or acute injury. It can also be used to treat menstrual pain and dysmenorrhea.

Many diclofenac formulations to be taken orally comprise an enteric coating, which minimises direct contact between the drug and the gastric mucosa. It is known that diclofenac is poorly soluble in the stomach due to the acid pH, but more soluble in the alkaline pH of the duodenum. In this manner many such formulations are generally designed to delay release until the formulation passes through the stomach.

U.S. Pat. No. 6,312,724 describes a sustained release formulation comprising diclofenac.

It is amongst the objects of the present invention to obviate and/or mitigate at least one of the aforementioned disadvantages.

It is amongst the objects of the present invention to provide a formulation which may be easily and/or cheaply manufactured and which allows for an active agent to be administered immediately and following a period of delay following administration.

SUMMARY OF INVENTION

The present inventors recognised a need to be able to administer, for example, a pharmaceutically active agent to a subject in a manner such that an immediate and a delayed release of the pharmaceutically active ingredient could be achieved. Although this may have been possible using prior device/methods known in the art, many such devices/methods were highly complex and there is distinct advantage in providing a simpler press-coated tablet formulation.

One particularly preferred embodiment relates to treating subjects with arthritis or acute pain who may suffer pain before going to bed and would also suffer pain/inflammation on waking. In a preferred embodiment therefore, the formulations of the present invention are for alleviating pain due to, for example, arthritis or acute injury. Such formulations therefore comprise a pharmaceutically active agent for alleviating pain/inflammation associated with arthritis or other conditions. Typically this may be a NSAID, such as diclofenac.

Thus, in a first aspect, the present invention provides a NSAID agent such as diclofenac, formulated as a component of a press-coated tablet for alleviating pain and/or inflammation, wherein the tablet is intended to be administered immediately prior to a subject going to sleep (i.e. when a subject goes to bed at night for a prolonged period of sleep, such as 6-10 hours and hence is distinguished over shorter sleeping periods) and wherein a portion of the NSAID is initially to be released immediately following administration and a further portion is released following a period of delay after administration.

In a further aspect there is provided a method of alleviating pain and/or inflammation such as associated with arthritis, the method comprising administering a press-coated tablet comprising an NSAID(s), such as diclofenac to a subject, immediately before the subject intends sleeping, wherein the formulation releases an NSAID immediately following administration and further releases an NSAID following a period of delay after administration of the tablet.

It is to be appreciated that said NSAIDs may be in respect of the same drug, or different drugs. Thus, for example, the first portion may release a first NSAID and the second portion may release a different or the same NSAID.

The immediate release of the active agent may be realised by way of a top-coating layer comprising an amount of the active agent together with one or more excipients therefore.

By "immediately" is understood to mean that at least 70-90%, such as 80% of the active agent in the top layer or portion of the press-coated tablet which is formulated for immediate release is released within about 5-45 mins, such as 10-30 mins following administration and the further portion is released after a period of delay which is typically from 3-8 hours following administration.

Typically delayed release of the active agent is achieved by providing a press-coated tablet comprising a delayed release layer surrounding a core comprising the active agent. The delayed release layer may comprise a wax and LH-32.

In a further aspect, the present invention provides a press-coated tablet formulation for an immediate, followed by a delayed release of an active agent, the tablet comprising (a) a core comprising an active agent together with an excipient(s); and
(b) a delayed release layer surrounding the core and comprising a wax and LH-32 in a ratio of 40:60 to 60:40 w/w; wherein the delayed release layer substantially delays release of the active agent within the core for between 3-8 hours after administration of the tablet by a subject and thereafter a pulsed release of the active agent from the core occurs, such that substantially all (typically greater than 90%, 95%, or even 99%) of the active agent in the core is released within 5-45 mins, such as 10-30 mins; and
(c) a top-coating layer comprising a portion of an active agent together with one or more excipients wherein a substantially immediate pulsed release of the active agent occurs following administration to the subject of the tablet. Delayed Release is More Preferably for 4-7 Hours Following Administration.

The active agents of the above aspect may be the same or different and include any active agent for which delayed followed by pulsed release is desirable. In a preferred embodiment of the invention, the active agent is a pharmaceutically acceptable active agent and includes pharmaceutical and veterinary active agents (often referred to as drugs). In other embodiments, the active agent includes agrichemical agents (such as fertilizers, herbicides, pesticides and fungicides), active agent used in the exterminating industry (such as toxins and poisons), and active agents used in industrial manufacturing (such as catalysts or catalytic quenchers).

Exemplary active agents for use in the pharmaceutical and veterinary applications of the invention include analgesics, anti-inflammatories, anesthetics, anticonvulsants, antidiabetic agents, antihistamines, anti-infectives, antineoplastics, antiparkinsonian agents, antirheumatic agents, appetite stimulants, appetite suppressants, blood modifiers, bone metabolism modifiers, cardiovascular agents, central nervous system depressants, central nervous system stimulants, decongestants, dopamine receptor agonists, electrolytes, gastrointestinal agents, immunomodulators, muscle relaxants, narcotics, parasympathomimetics, sympathomimetics, sedatives, and hypnotics.

The press-coated tablets of the present invention may be used to treat one or more of the following conditions/disorders or diseases:
Central Nervous System disorders, e.g. Neurogenic pain, stroke, dementia, Alzheimer's disease, Parkinson's disease, neuronal degeneration, meningitis, spinal cord injury, cerebral vasospasm, amyotrophic lateral sclerosis
Cardiovascular disease, hypertension, atherosclerosis, angina, arterial obstruction, peripheral arterial disease, myocardial pathology, Arrhythmia, Acute Myocardial Infarction, Angina, Cardiomyopathy, Congestive heart failure, Coronary artery disease (CAD), Carotid artery disease, Endocarditis, Hypercholesterolemia, hyperlipidemia, Peripheral artery disease (PAD)
Genitourinary Disorders; erectile dysfunction, urinary organ diseases benign prostatic hypertrophy (BPH), Renal tubular acidosis, diabetic nephropathy, glomerulonephritis, glomerulosclerosis, urinary tract infection, faecal incontinence
Ocular disease glaucoma, blephartitis, ocular hypertension, retinopathy, conjunctivitis, scleritis, retinitis, keratitis, corneal ulcer, iritis, Chorioretinal inflammation, macular edema, Xerophthalmia
Pulmonary disease asthma, pulmonary hypertension, acute respiratory distress syndrome, COPD, emphysema, pneumonia, tuberculosis, bronchitis, Acute Bronchitis, Bronchiectasis, Bronchiolitis, Bronchopulmonary Dysplasia, Byssinosis, Coccidioidomycosis (Cocci), Cystic Fibrosis, Influenza, Lung Cancer, Mesothelioma
Metabolic diseases; Hypercalciuria, Hyperglycemia, Hyperinsulinemic hypoglycemia, Hyperinsulinism, Hyperlysinuria, Hypoglycemia
Exocrine and Endocrine; Addison's disease, Hypoaldosteronism, cushing's syndrome, diabetes, Goitre, Hyperthyroidism, Hypothyroidism, Thyroiditis, pancreatitis
Hepatic disorders, Hepatitis, Non-alcoholic fatty liver disease, cirrhosis, hepatic cancer, Primary sclerosing cholangitis, primary biliary cirrhosis, Budd-Chiari syndrome,
Autoimmune and Inflammatory diseases, multiple sclerosis rheumatoid arthritis, psoriasis, diabetes, sarcoidosis, Addison's Disease, Alopecia areata, Amyotrophic Lateral Sclerosis, Ankylosing Spondylitis, polyarticular Arthritis, Atopic allergy, topic Dermatitis, Autoimmune hepatitis, Celiac disease, Chagas disease, Coeliac Disease, Cogan syndrome, Crohns Disease, Cushing's Syndrome, Diabetes mellitus type 1, Endometriosis, Eosinophilic fasciitis, Fibromyalgia/Fibromyositis, Gastritis, Glomerulonephritis, Graves' disease. Guillain-Barre syndrome (GBS), Hashimoto's encephalitis, Hashimoto's thyroiditis, Haemoiytic anaemia, idiopathic inflammatory Demyelinating Diseases, Idiopathic pulmonary fibrosis, interstitial cystitis, Juvenile idiopathic arthritis, Juvenile rheumatoid arthritis, Kawasaki's Disease, Lichen sclerosus, Lupus erythematosus, Meniere's disease, Myasthenia gravis, myositis, Narcolepsy, Pernicious anaemia, Perivenous encephalomyelitis, Polymyalgia rheumatica, Primary biliary cirrhosis, Psoriatic Arthritis, Reiter's syndrome, Rheumatoid fever, Sarcoidosis, Schizophrenia, Sjogren's syndrome, Spondyloarthropathy, Ulcerative Colitis
Musculoskeletal disorders: osteoarthritis, osteoporosis, Osteonecrosis, Arthritis, Paget's Disease Bursitis, Costochondritis, Tendonitis
Skin disorders; Acne, alopecia, candidiasis, cellulitis, dermatitis, eczema, epidermolysis bullosa, erythrasma, herpes, erysipelas, Folliculitis, impetigo, ringworm, scabies, Tinea, Trichomycosis
ENT disorders; Otitis, sinusitis, laryngitis, pharyngitis, laryngitis, meniere's disease, labyrinthitis,
Others: acute and chronic pain, viral infection, cancer, laryngitis, mastoiditis, myringitis, otitis media, rhinitis, sinusitis, Sialadenitis, Retropharyngeal Abscess, Tonsillopharyngitis,
Gastro-Intestinal Disorders
Irritable bowel syndrome (IBS) necrotizing entercolitis (NEC) non-ulcer dyspepsia, chronic intestinal pseudo-obstruction, functional dyspepsia, colonic pseudo-obstructioduodenogastric reflux, gastroesophageal reflux disease, ileus inflammation, gastroparesis, heartburn, constipation—(e.g. constipation associated with use for medications such as opioids), colorectal cancer, colonic polyps, diverticulitis, colorectal cancer, Barretts Esophagus, Bleeding in the Digestive Tract, Celiac Disease, Colon Polyps, Constipation, Crohns DiseaseACyclic Vomiting Syndrome, Delayed Gastric Emptying (Gastroparesis), Diarrhea, Diverticulosis, Duodenal Ulcers, Fecal Incontinence, Gallstones, Gas in the Digestive Tract, Gastritis, Gastroesophageal Reflux Disease (GERD), Heartburn^Hiatal Hernia, Hemochromatosis, Hemorrhoids, Hiatal Hernia, Hirschsprung's Disease, Indigestion, Inguinal Hernia, Lactose Intolerance, Peptic Ulcers, Polyps, Porphyria, Primary Biliary Cirrhosis, Primary Sclerosing Cholangitis, Proctitis, Rapid Gastric Emptying, Short Bowel Syndrome, Stomach Ulcers, Ulcerative Colitis, Uicers, whippies Disease Said Active Agent or Agents May be Selected from the Following:

Gastro Drugs

Antacids—aluminium hydroxide, magnesium carbonate, magnesium trisilicate, hydrotalcite, simeticonealginates, Antispasmodics—atropine sulphate, dicycloverine hydrochloride, hyoscine butylbromine, propantheline bromide, alverine citrate, mebeverine hydrochloride, Motility stimulants—metoclorpramide, domperidone H2-Receptor antagonists—Cimetidine, famotidinenizatidine, ranitidine Antimuscarinics—pirenzepine Chelates—Tripotassium dicitratbismuthate, sucralfate, Prostaglandin analogues—misoprostol Aminosalicylates—balsazide sodium, mesalazine, olsalazine, sulphasalazine Corticosteroids—beclometasone dipropionate, budenoside, hydrocortisone, prednisolone, Affecting immune response—ciclosporin, mercaptopurine, methotrexate, adalimumab, infliximab Stimulant Laxatives—bisacodyl, dantron, docusate, sodium picosulfate, Drugs affecting biliary composition and flow—ursodeoxycholic acid Bile acids sequestrants—colestyramine, Oxyphencyclimine, Camylofin, Mebeverine, Trimebutine, Rociverine, Dicycloverine, Dihexyverine, Difemerine, Piperidolate Benzilone, Mepenzolate, Pipenzolate, Glycopyrronium, Oxyphenonium, Penthienate, Methantheline, Propantheline, Otilonium bromide, Tridihexethyl, Isopropamide, Hexocyclium, Poldine, Bevonium, Diphemanil, Tiemonium iodide, Prifinium bromide, Timepidium bromide, Fenpiverinium Papaverine, Drotaverine, Moxaverine 5-HT3 antagonists (Alosetron, Cilansetron), 5-HT4 agonists (Mosapride, Prucaiopride, Tegaserod) Fenpiprane, Diisopromine, Chiorbenzoxamine, Pinaverium, Fenoverine, Idanpramine, Proxazole, Alverine, Trepibutone, Isometheptene, Caroverine, Phloroglucinol, Silicones, Trimethyldiphenylpropylamine Atropine, Hyoscyamine Scopolamine (Butylscopolamine, Methylscopolamine), Methylatropine, Fentonium, Cimetropium bromide primarily dopamine antagonists (Metoclopramide/Bromopride, Cleboride, Domperidone, Alizapride), 5-HT4 agonists (Cinitapride, Cisapride), Proton pump inhibitors Omeprazole, lansoprazole, pantoprazole, esomeprazole, rabeprazole sodium, opioids and opiod receptor antagonists—e.g. codeine, morphine, loperamide, diphenoxylate, methylnaltrexone bromide Analgesic Acetaminophen Diclofenac Diflunisal Etodolac Fenoprofen Flurbiprofen Ibuprofen Indomethacin Ketoprofen Ketorolac Meclofenamate Mefenamic Acid Meloxicam Nabumetone Naproxen Oxaprozin Phenylbutazone Piroxicam Sulindac Tolmetin Celecoxib Buprenorphine Butorphanol Codeine Hydrocodone Hydromorphone Levorphanol Meperidine Methadone Morphine Nalbuphine Oxycodone Oxymorphone Pentazocine, Propoxyphene Tramadol codeine Sleep drugs Hypnotics—Nitrazepam, Flurazepam, Loprazolam, Lormetazepam, Temazepam, Zaleplon, Zolpidem, Zopiclone, Chloral Hydrate, Triclofos, Clomethiazole, Quazepam, triazolam Estazolam Clonazepam, Alprazolam, Eszopiclone, Rozerem, Trazodone, Amitriptyline Doxepin, Benzodiazepine drugs, melatonin, diphenhydramine and herbal remedies such as Valerian Cardiovascular Medicines Cardiac glycosides—Digoxin, digitoxin, Phosphodiesterase Inhibitors—enoximone, milrinone Thiazides and related diuretics—bendroflumethiazide, chlortalidone, cyclopenthiazide, inapamide, metolazone, xipamide Diuretics—furosemide, bumetanide, torasemide, Potassium sparing diuretics and aldosterone antagonists—amiloride hydrochloride, triamterene, weplerenone, spironolactone, Osmotic diuretics—mannitol Drugs for arrhythmias—adenosine, amiodarone hydrochloride, disopyramide, flecainide acetate, propafenone hydrochloride, lidocaine hydrochloride, Beta adrenoreceptor blocking drugs—propanalol, atenolol, acebutolol, bisprolol fumarate, carvedilol, celiprolol, esmolol, lebatolol, metoprolol tartrate, nadolol, nebivolol, oxprenolol, pindolol, solatol, timolol, Hypertension—ambrisentan, bosentan, diazoxide, hydralazine, iloprost, minoxidil, sildenafil, sitaxentan, sodium nitroprusside, clonidine, methyldopa, moxonidine, guanethidine monosulphate, doxazosin, indoramin, prazosin, terazosin, phenoxybenzamine, phentolamine mesilate, Drugs affecting the renin-angiotensin system—Captropril, Cilazapril, Enalapril Maleate, Fosinopril, Imidapril, Lisinopril, Moexipril, Perindopril Erbumine, Quinapril, Ramipril, Trandolapril, Candesartan Cilexetil, Eprosartan, Irbesartan, Losartan, Olmesartan Medoxomil, Telmisartan, Valsartan, Aliskiren.

Nitrates, calcium channel Blockers and antianginal drugs—Glyceryl trinitrate, Isosorbide Dinitrate, Isosorbide Mononitrate, Amlodipine, Diltiazem, Felodipine, Isradipine, Lacidipine, Lercanidipine, Nicardipine, Nifedipine, Nimodipine, Verapamil, Ivabradine, Nicorandil, Ranolazine, Peripheral Vasodilators and related drugs—Cilostazol, Inositol Nicotinate, Moxisylyte, Naftidrofuryl Oxalate, Pentoxifylline, Sympathomimetics—Dopamine, Dopexamine, Ephedrine, Metaraminol, Noradrenaline Acid Tartrate, Norephidrine Bitartrate, Phenylephidrine, Anticoagulants and Protamine—Heparin, Bemiparin, Dalteparin, Enoxaparin, Tinzaparin, Danaparoid, Bivalirudin, Lepirudin, Epoprostenol, Fondaprinux, Warfarin, Acenocoumarol, Phenindione, Dabigatran Etexilate, Rivaroxaban, Protamine Sulphate, Antiplatelet Drugs—Abciximab, Asprin, Clopidogrel, Dipyridamole, Eptifibatide, Prasugrel, Tirofiban, Fibrinolytic and antifibrinolytic Drugs—Alteplase, Reteplase, Streptokinase, Tenecteplase, Urokinase, Etamsylate, Tranexamic Acid, Lipid Regulating Drugs—Atorvastatin, Fluvastatin, Pravastatin, Rosuvastatin, Simvastatin, Colesevam, Colestyramine, Colestipol, Ezetimibe, Bezafibrate, Ciprofibrate, Fenofibrate, Gemfibrozyl, Acipmox, Nictotinic Acid, Omega three fatty acid compounds, Ethanolamine Oleate, Sodium Tetradecyl Suphate.

CNS Drugs—Benperidol, Chlorpromazine, Flupentixol, Haloperidol, Levomepromazine, Pericyazine, Perphenazine, Pimozide, Prochlorperazine, Promazine, Sulpiride, Trifluoperazine, Zuclopenthixol, Amisulpride, Aripiprazole, Clozapine, Olanzapine, Paliperidone, Quetiapine, Riperidone, Sertindole, Zotepine, Flupentixol, Fluphenazine, Olanzapine Embonate, Pipotiazine Palmitate, Risperidone, Zuclopenthixol Decanoate, Carbamazepine, Valproate, Valproic acid, Lithium Carbonate, Lithium Citrate, Amitriptyline, Clomipramine, Dosulepin, Imipramine, Lofepramine, Nortriptyline, Trimipramine, mianserin, Trazodone, Phenelzine, Isocarboxazid, Tranylcypromine, Moclobemide, Citalopram, Escitalopram, Fluoxetine, Fluvoxamine, Paroxetine, Sertraline, Agomelatine, Duloxetine, Flupentixol, Mirtazapine, Reboxetine, Trytophan, Venflaxine, Atomoxetine, Dexametamine, Methylphenidate, Modafinil, Eslicarbazepine, Ocarbazepene, Ethosuximide, Gabapentin, Pregabalin, Lacosamide, Lamotrigine, Levetiracetam, Phenobarbital, Primidone, Phenytoin, Rufinamide, Tiagabine, Topiramate, Vigabatrin, Zonisamide, ropinirole, Rotigotine, Co-Beneldopa, Levodopa, Co-Careldopa, Rasagiline, Selegiline, Entacapone, Tolcapone, Amantidine, Orphenadrine, Procyclidine, Trihexyphenidyl, Haloperidol, Piracetam, Riluzole, Tetrabenazine, Acamprosate, Disulfiram, Bupropion, Vareniciline, Buprenorphine, Lofexidine, Donepezil, Galantamine, Memantine, Rivastigimine.

Anti-Infectives—Benzylpenicillin, Phenoxymethylpenicillin, Flucloxacillin, Temocillin, Amoxicillin, Ampicillin, Co-Amoxiclav, Co-Fluampicil, Piperacillin, Ticarcillin, Pivmecillinam, Cephalosporins, Cefaclor, Cefadroxil, Cefalexin, Cefixime, Cefotaxime, Cefradine, Ceftazidime, Cefuroxime, Ertapenem, Imipenem, Meropenem, Aztreonam, Tetracycline, Demeclocycline, Doxocycline, Lymecycline, Minocycline, Oxytetracycline, Tigecycline, Gentamicin, Amikacin, Neomycin, Tobramycin, Erythromycin, Azithromycin, Clarithromycin, Telithromycin, Clindamycin, Chloramphenicol, Fusidic Acid, Vancomycin, Teicoplanin, Daptomycin, Linezolid, Quinupristin, Colistin, Co-Trimoxazole, Sulpadiazine, Trimethoprim Capreomycin, Cycloserine, Ethambutol, Isoniazid, Pyrazinamide, Rifabutin, Rifampicin, Streptomycin, Dapsone, Clofazimine, Metronidazole, Tinidazole, Ciproflaxacin, Levoflaxacin, Moxifloxacin, Nalidixic Acid, Nortlaxine, Orliaxacin, Nitrofurantoin, Methenamine Hippurate, Amphotericin, Anidulafungin, Caspofungin, Fluconazole, Flucytosine, Griseofluvin, ltraconzole, Ketoconazole, Micafungin, Nystatin, Posaconazole, Terbinafine, Voriconazole, Abacavir, Didanosine, Emtricitabine, Lamivudine, Stavudine, Tenofovir Disoproxil, Zidovudine, Atazanavir, Darunavir, Fosamprenavir, Indinavir, Lopinair, Nelfinavir, Ritonavir, Saquinavir, Tipranavir, Efavirenz, Etravirine, Nevarapine, Enfuvirtide, Maraviroc, Raltegravir, Aciclovir, Famciclovir, Inosine Pranobex, Valaciclovir, Cidofovir, Gangciclovir, Foscarnet, Valgangciclovir, Adefovir Dipivoxil, Entecavir, Telbivudine, Amantadine, Oseltamivir, Zanamivir, Palivizumab, Ribavirin, Artemether, Chloroquine, MefloquinePrimaquine, Proguanil, Pyrimethamine, Quinine, Doxycyclin, Diloxanide Furoate, Metronidaziole, Tinidazole, Mepacrine-Sodium Stibogluconate, Atovaquone, Pentamidine Isetionate, Mebendazole, Piperazine, Other:
Benztropine, procyclidine, biperiden, Amantadine, Bromocriptine, Pergolide, Entacapone, Tolcapone, Selegeline, Pramipexole, budesonide, formoterol, quetiapine fumarate, olanzapine, pioglitazone, montelukast, Zoledromic Acid, valsartan, latanoprost, Irbesartan, Clopidogrel, Atomoxetine, Dexamfetamine, Methylphenidate, Modafinil, Bleomycin, Dactinomycin, Daunorubicin, Idarubicin, Mitomycin, Mitoxantrone, Azacitidine, Capecitabine, Cladribine, Clofarabine, Cytarabine, Fludarabine, Flourouracil, Gemcitabine, mercaptopurine, methotrexate, Nelarabine, Pemetrexed, Raltitrexed, Thioguanine, Apomorphine, Betamethasone, Cortisone, Deflazacort, Dexamethosone, Hydrocortisone, Methylprednisolone, Prednisolone, Triamcinolone, Ciclosporine, Sirolimus, Tacrolimus, Interferon Alpha, Interferon Beta.

In a particularly preferred embodiment the active agent is designed to treat arthritis and/or acute pain and as such the active agent is preferably an NSAID, such as diclofenac.

The term "active agent" is understood to include solvates (including hydrates) of the free compound or salt, crystalline and non-crystalline forms, as well as various polymorphs. For example, the active agent can include all optical isomers of the compounds and all pharmaceutically acceptable salts thereof either alone or in combination threo isomers can be indicated as "threo" and the combined erythro isomers as "erythro".

In accordance with the invention, formulations are provided which are to be taken by a subject and which initially administer a portion of the active agent when the subject first takes the formulation and moreover at a later time point a further portion of the agent is administered to the subject. Preferably the immediate and/or delayed administration may be by way of a pulsed dose, where said portion of active agent is substantially delivered within about 5-45 mins, such as 10-30 mins.

The present inventors identified the need to be able to administer a pain relieving/anti-inflammatory drug to a subject before the subject went to bed, but recognised that often subjects feel pain immediately upon waking and if they were to take pain relief once awake, there would be a period of time when they suffered pain. The present inventors therefore developed formulations which as well as delivering pain/anti-inflammatory relief prior to sleep, also deliver pain/anti-inflammatory relief shortly before waking and hence serve to improve pain management by the subject.

LH-32 is a particular type of low substituted hydroxypropyl cellulose (L-HPC) and may be obtained from Shin-Etsu Chemical Co., Ltd., Tokyo, Japan. L-HPCs are insoluble in water and comprise a glucose backbone which is substituted to a minimal extent by hydroxypropyl groups. LH-32 is micronised, with a mean particle diameter of 20 Qm LH-32 has a molecular weight of around 115,000 and a hydroxypropyl cellulose content of around 8%.

The wax may be any suitable wax such as beeswax, carnuba wax, microcrystalline wax, hydrogenated castor oil. A particularly preferred wax is a glyceryl ester, such as glycerol behenate.

In a preferred formulation of the present invention as defined herein above, the wax and LH-32 are present in a ratio of 40:60 to 60:40 w/w. More preferably the ratio is 45:55 to 55:45 w/w, or 50:50 w/w. The skilled addressee will appreciate that with appropriate variation of the ratio, the delay in drug release can be tailored for a particular application. For example, a 50:50 w/w ratio of glycerol behenate as a wax, with LH-32 employed as a delayed release layer in accordance with the present invention, is observed to provide a delayed release of approximately 6 hours. However, the same ratio with LH-21 as the L-HPC provides a delay in release of oniy 2 hours. Thus with appropriate control of the ratio of wax to L-HPC and the type of wax/L-HPC, it is possible to control the time delay in release of the active agent, from a press-coated tablet comprising a delayed release layer surrounding a core comprising the active agent.

The delayed release layer surrounding the core may also comprise an amount of an active agent or agents, which may be the same or different to the active agent in the core and/or top layer, and which is designed to be released during dissolution/disintegration of the delayed release layer.

The top layer comprises an active ingredient for immediate release and generally comprises one or more excipients, such as a sugar and/or an L-HPC.

The subject to be treated is an animal, e.g. a mammal, especially a human.

The amount of active agent to be administered will be sufficient to be therapeutic or prophylactic. By therapeutic or prophylactic is meant one capable of achieving the desired response, and will be adjudged, typically, by a medical practitioner. The amount required will depend upon one or more of at least the active compound(s) concerned, the patient, the condition it is desired to treat or prevent and the formulation. However, it is likely to be in the order of from 1 μg to 1 g of compound per kg of body weight of the patient being treated.

Different dosing regimes may likewise be administered, again typically at the discretion of the medical practitioner. The formulation of the present invention may allow for at least daily administration although regimes where the compound(s) is (or are) administered more infrequently, e.g. every other day, weekly or fortnightly, for example, are also embraced by the present invention.

By treatment is meant herein at least an amelioration of a condition suffered by a patient; the treatment need not be curative (i.e. resulting in obviation of the condition). Analogously references herein to prevention or prophylaxis herein do not indicate or require complete prevention of a condition; its manifestation may instead be reduced or delayed via prophylaxis or prevention according to the present invention.

For use according to the present invention, the compounds or physiologically acceptable salt, solvate, ester or other physiologically acceptable functional derivative thereof described herein are presented in a press-coated tablet form comprising the compound or physiologically acceptable salt, ester or other physiologically functional derivative thereof, together with one or more pharmaceutically acceptable excipients therefore and optionally other therapeutic and/or prophylactic ingredients. Any excipients are acceptable in the sense of being compatible with the other ingredients of the formulation and not deleterious to the recipient thereof.

The tablets of the present invention may be prepared using reagents and techniques readily available in the art and/or exemplary methods as described herein.

The tablets include those suitable for oral, rectal or vaginal administration. The tablets may, where appropriate, be conveniently presented in discrete dosage units and may be prepared by any of the methods well known in the art of pharmacy.

Compressed tablets may be prepared by compressing in a suitable machine an active compound in a free-flowing form such as a powder or granules optionally mixed with a binder, lubricant, inert diluent, lubricating agent, surface-active agent or dispersing agent, together with the materials for forming the delayed release layer. The tablets also comprise a top-coat comprising a portion of the active agent for immediate release.

Tablets suitable for rectal administration are most preferably presented as unit dose suppositories. Suitable carriers include cocoa butter and other materials commonly used in the art. The suppositories may be conveniently formed by admixture of a tablet with the softened or melted carrier(s) followed by chilling and shaping in moulds.

The tablets of the present invention may be prepared using pharmaceutical processes namely by direct compression or by granulation processing and final tableting. The process may comprise the steps of initially forming a core comprising the active agent and subsequently surrounding core with the delayed release layer and a further top layer. The core may be formed by dispersing one or more active agents with one or more excipients, such as a sugar, microcrystalline cellulose talc, dicalcium phosphate and the like.

The delayed release layer may be formed by melting the wax component and subsequently admixing the other components including the LH-32. The mixture may then be allowed to cool and solidify before being ground and/or forced through a sieve, in order to achieve granules of the size range 500 Qm-1 mm. The core may then be coated with the delayed release layer material by direct compression. Typically the core is sandwiched between top and bottom layers of the delayed release material and hence completely surrounds the core.

At the same time, the top-coating layer may be press-coated on top of the delayed release layer. The top-coating may be formed by blending together the active agents and one or more excipients, such as a sugar (e.g. lactose) and a L-HPC, such as LH-21.

The tableting for the formulation of tablets may be conducted using an apparatus ordinarily employed for the formation or granulation of tablets. Examples may include single-punch tableting machine, rotary tableting machine and tableting tester.

Tableting is conducted usually under a pressure of 50 to 300 MPa, preferably 80 to 200 MPa. At a pressure less than 50 MPa, the resulting tablet may have insufficient hardness, which disturbs easily handling, while pressures exceeding 300 MPa may serve to cause a delay in disintegration.

The core, delayed release layer and/or top-coating layer may include a filler, such as a water insoluble filler, water soluble filler, and mixtures thereof. The water insoluble filler, may be a calcium salt or talc. Exemplary water soluble fillers such as water soluble sugars and sugar alcohols, preferably lactose, glucose, fructose, mannose, galactose, the corresponding sugar alcohols and other sugar alcohols, such as mannitol, sorbitol, and xylitol.

The filler in one of the layers can be the same or different as the filler in another layer, if any. For example, the core composition can include a water-soluble filler while the top-coat composition can include a water insoluble filler.

Other excipients can also be present in the core delayed release layer and/or top-coating layer, including lubricants (such as talc and magnesium stearate), glidants (such as fumed or colloidal silica), pH modifiers (such as acids, bases and buffer systems), and pharmaceutically useful processing aids. It will be appreciated that such other excipients may be the same or different in the core and delayed release layer, if any.

In a preferred embodiment of the invention, the core components (active agent and optional excipients) are blended together and compressed into suitable cores. The blending can take place in any order of addition. Preferably, the cores are blended by starting with the smallest volume component and then successively adding the larger volume components.

DETAILED DESCRIPTION

The present invention will now be further described by way of example and with reference to the figures which show:

Figure 3:
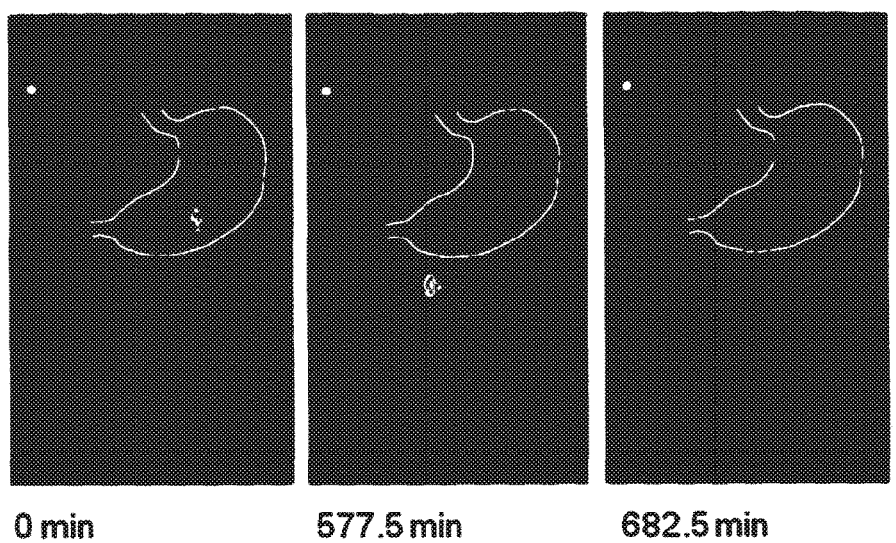
Figure 4:
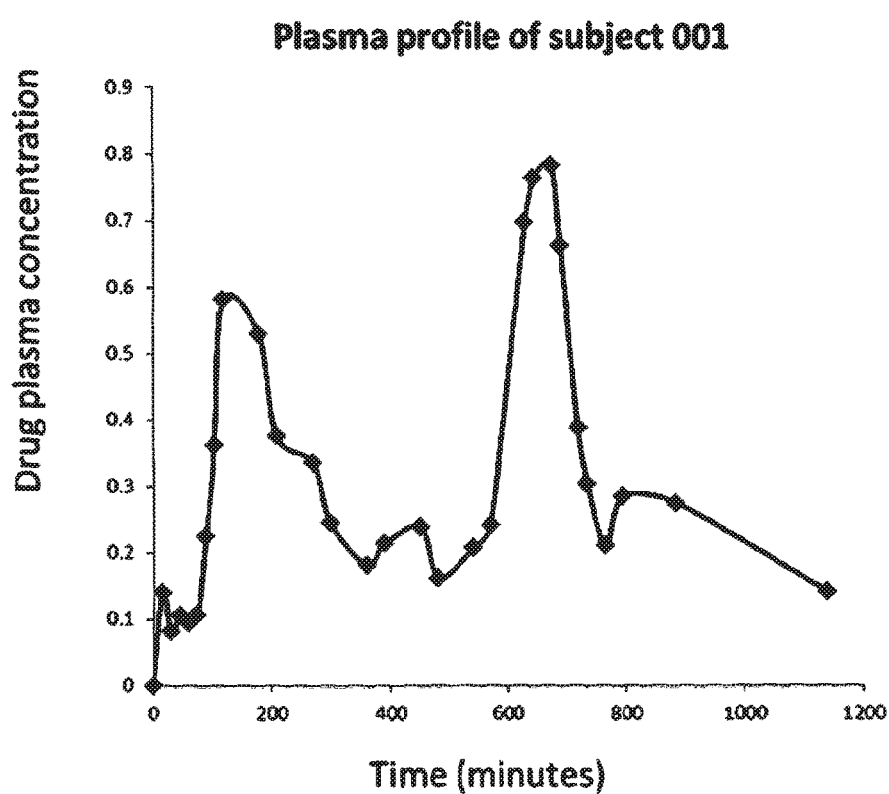

FIG. 3 shows Gamma Scintigraphy imaging of In-vivo release of controlled release Diclofenac formulation. Radiolabel was incorporated in the delayed release layer only and so only the delayed release is being visualised; and FIG. 4 shows the analysis of blood plasma levels of Diclofenac following administration of a controlled release formulation of Diclofenac, there is a period of time between drug release and detection in blood plasma as the drug is solubilised and absorbed by the body.

CLINICAL NEED

This formulation is designed to relieve night-time pain (e.g. in arthritic patients) by releasing an immediate burst of diclofenac and then another after six hours.

Methods

Core Tablet Blend and Core Tablet Compression (MW Diclofenac=296.2 and MW Diclofenac sodium=318.1)

(i) Diclofenac and excipients weighed into tared weigh boats and all except the magnesium stearate placed into an amber screw-top glass jar of sufficient volume (e.g. 125 ml) according to Table 1.

TABLE 1

| API/Excipient | Weight (g) |
| --- | --- |
| Diclofenac sodium | 5.4 |
| Ac-di-sol | 1.3 |
| Lactose | 1.7 |
| Magnesium stearate | 0.6 |

(ii) These API/excipients blended (in the glass jar) using the Turbula mixer for 1 minute.

(iii) Magnesium stearate added and all blended for further 5 minutes 90 mg of this blend comprises each core tablet. 90 mg weighed into a tared weigh boat.

(iv) The 6.9 mm punch and die set used to compress 90 mg powder for 10 seconds at 1 ton using the IR press.

(v) Tablets stored in an amber glass screw-top jar until use.

Granules (to Surround Core Tablet)

(i) Glycerol behenate and LH-32 weighed into tared weigh boats according to Table 2:

TABLE 2

| Excipient | Weight (g) |
| --- | --- |
| GB | 10 |
| LH-32 | 10 |

(ii) GB placed in a glass beaker on a hot plate set at 100° C. Once the GB melted, LH-32 added gradually whilst stirring until a uniform mix is achieved.

(iii) The mix stirred continuously until cooled to room temperature. The granules are left for at least 30 min at room temperature before the next step.

(iv) The cooled granules forced through a 1 mm sieve (using a spatula and a brush) and collected on a 500μm sieve so that the granules used are in the size range 500μm∩-1 mm.

(v) Granules stored in amber glass screw-top jar until use.

Top Layer Blend

Diclofenac and excipients are weighed into tared weigh boats and all placed into an amber screw-top glass jar of sufficient volume (eg 125 ml) according to Table 3.

TABLE 3

| API/Excipient | Weight (g) |
| --- | --- |
| Diclofenac sodium | 10.8 |
| Lactose | 8.6 |
| LH-21 | 8.6 |

The API/excipients blended (in the glass jar) using the Turbula mixer for 15 minutes.

Formulation Compression (i) A 13 mm die and matching flat-faced punches were used to compress the formulation. For 6 tablets, 12×250 mg granules (to surround core tablet) are weighed into tared weigh boats.

(ii) 250 mg granules placed onto the lower punch, core tablet dropped on and centralised (centralising tool) before placing the other 250 mg granules on top.

(iii) For 6 tablets, 6×140 mg top layer blend weighed into tared weigh boats.

(iv) 140 mg of the top layer blend added to the top granule layer.

(v) The formulation compressed at 5 ton for 3 minutes in a 13 mm die/punch set.

Dissolution

Dissolution (n=3) performed in 900 ml sodium phosphate buffer (0.01 M, pH 7) at 37° C., with UV analysis at 248 nm.

Results

Figure 1:
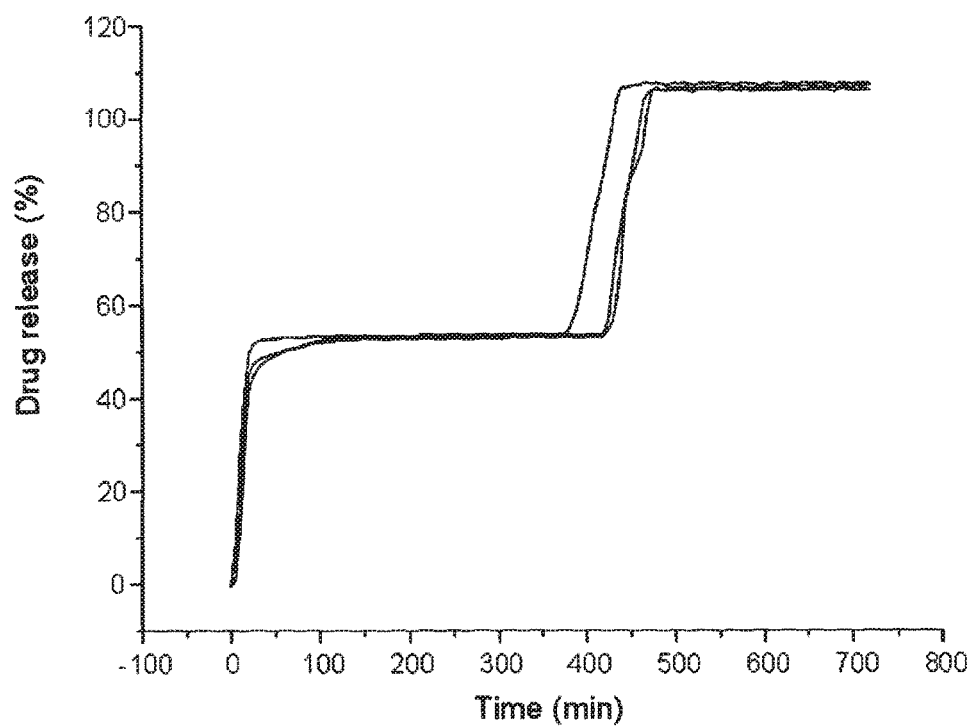
FIG. 1 shows the release profile of a tablet formulation comprising an immediate release top-coating and a delayed release layer of 50:50 w/w glycerol behenate: LH-32.

As can be seen in FIG. 1, a tablet is provided which provides an initial release of diclofenac, over about 10 minutes, followed by a delay of about 5.5. hours and a further release of diclofenac over about 30-40 mins.

Supporting Data

Figure 2:
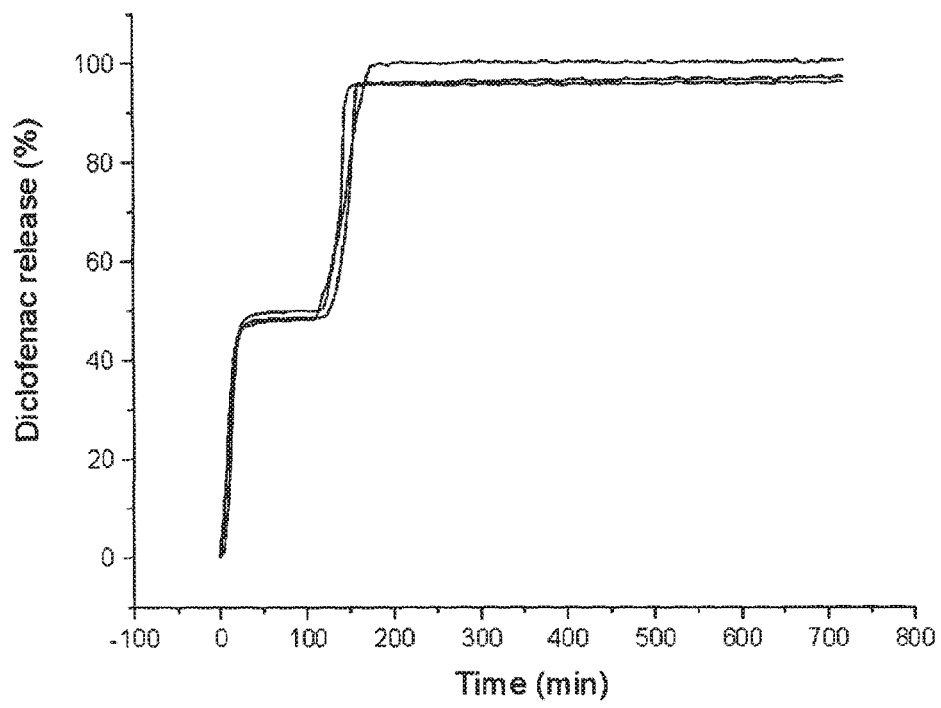
FIG. 2 shows the release profile of a tablet formulation comprising an immediate release top-coating and a delayed release layer of 50:50 w/w glycerol behenate: LH-21.

This profile in FIG. 2 shows a dramatically shortened time between pulses of diclofenac e.g. with LH-21 instead, as compared to that with LH-32, thus rendering it inappropriate for the desired clinical application.

Clinical Trial Protocol

Diclofenac 50 mg immediate-release with diclofenac 50 mg delayed-release (6 hour time-delay)

Diclofenac Extraction from Plasma Calibration and Calculation of % Recovery

Preliminary Preparation:

1. Preparation of 100 ml stock solution of 3M Orthophosphoric acid (H3PO4. 98 g/mol)
   (i) Using an 85% solution (VWR).
   (ii) 3M=294 g/L, therefore 29.4 g in 100 ml.
   (iii) Take 34.6 ml of the 85% VWR solution and make up to 100 ml with water in a volumetric flask.
2. Preparation of 1 L stock solution of Hexane:IPA, 90:10.
   (i) Add 900 ml hexane and 100 ml IPA to a 1 L duran bottle. Wrap the top with parafilm for storage.
3. Ketoprofen (internal standard) stock solution (1 mg/ml)
   (i) Weigh 100 mg into a weigh boat and transfer to a 100 ml volumetric flask. Add 60 ml mobile phase and dissolve. Make up to the 100 ml mark with mobile phase.
4. Diclofenac stock solutions
   (i) Solution A: Weigh 100 mg diclofenac and make up to 100 ml with water in a volumetric flask (1 mg/ml).
   (ii) Solution B: Take 10 ml from Solution A and make up to 100 ml with water in a volumetric flask (100 μg/ml).
   (iii) Solution C: Take 10 μl of Solution A and make up to 1 ml with water (1 pg/ml).

Preparing the Standard Series of Diclofenac Solutions:

Add the required volume of either stock solution B or C to a small vial and make up to 1 ml with water as shown in the following table.

| Standard | Required Conc. (μg/ml) | Vol stock sol. (μl) | Vol H₂O (μl) | In 100 μl (ng) |
|---|---|---|---|---|
| 1 | 0.25 | 250 (C) | 750 | 25 |
| 2 | 0.5 | 500 (C) | 500 | 50 |
| 3 | 1.0 | 10 (B) | 990 | 100 |
| 4 | 2.5 | 25 (B) | 975 | 250 |
| 5 | 5.0 | 50 (B) | 950 | 500 |
| 6 | 10 | 100 (B) | 900 | 1000 |
| 7 | 20 | 200 (B) | 800 | 2000 |
| 8 | 30 | 300 (B) | 700 | 3000 |

Extraction Procedure:
(i) Add 1 ml blank plasma to each of 8 plastic 15 ml centrifuge tubes
(ii) Add 100 μl of the diclofenac stock solutions to each
(iii) Vortex for 1 min
(iv) Add 1 ml of 3M Orthophosphoric acid to each
(v) Add 5 ml of hexane:isopropyl alcohol, 90:10
(vi) Vortex for 3 min
(vii) Centrifuge at 2000 rpm for 3 min
(viii) Extract the top (solvent) layer and transfer to a clean centrifuge tube
(ix) Evaporate the solvent to dryness under nitrogen
(x) Reconstitute residue in 100 μl mobile phase
(xi) Add 10 μl internal standard stock solution to each
(xii) Vortex
(xiii) Inject 50

The on column mass for each sample is as follows:

| Sample | On column mass (ng) |
|---|---|
| 1 | 12.5 |
| 2 | 25 |
| 3 | 50 |
| 4 | 125 |
| 5 | 250 |
| 6 | 500 |
| 7 | 1000 |
| 8 | 1500 |

Clinical studies were carried out in Healthy male volunteers aged between 18-65 years inclusive with a body mass index (BMI) between 18.0 and 29.9 kg/m². Subjects received a standard dinner comprising roast chicken with salad, low fat yoghurt and one cup of decaffeinated tea, coffee or juice 2 hours prior to dosing.

Gastrointestinal transit of the delayed-release tablets was characterised by inclusion of a radiolabel marker, technetium-99m ($^{99m}$Tc), complexed with diethylenetriaminepentaacetic acid (DTPA) which prevents absorption from the gastrointestinal tract. The radiolabel is incorporated into the core tablet. Each tablet was radiolabelled with 4 MBq 99mTc-DTPA and administered with 240 ml of water at bedtime.

Scintigraphic imaging was performed using a Siemens E-Cam gamma camera fitted with a low-energy high-resolution collimator. Subjects were imaged in a standing position except during periods of sleep where the subjects were imaged lying down. Anterior static acquisitions of 25-second duration each were collected immediately after dosing then every 30 minutes until 3 hours post-dose then every 15 minutes until complete release of radiolabel marker.

A 5 mL pre-dose blood sample was taken from each subject 15 minutes before dosing. Following dosing blood samples were taken. Every 15 minutes until 2 hours post-dose then every 30 minutes until burst release observed by scintigraphy then every 15 minutes for 2 hours then every 30 minutes for 1 hour then hourly until end of study day (15 hours post-dose). See FIG. 3.

Blood samples were centrifuged at 2000 g for 10 minutes and the plasma fraction removed and stored at −20° C. for subsequent analysis. See FIG. 4.

The invention claimed is:

1. A press-coated tablet formulation for an immediate, followed by a delayed release of an active agent, the tablet comprising:
   (a) a core comprising an active agent together with an excipient(s); and
   (b) a delayed release layer surrounding the core and comprising a wax and a low substituted hydroxypropyl cellulose in a ratio of 40:60 to 60:40 w/w; wherein the delayed release layer substantially delays release of the active agent within the core for between 3-8 hours after administration of the tablet to a subject and thereafter a pulsed release of the active agent from the core occurs, such that at least 70% of the active agent in the core is released within 5-45 minutes and wherein the low substituted hydroxypropyl cellulose is micronized with a mean particle diameter of 20 mm and has a molecular weight of 115,000 and a hydroxypropyl cellulose content of 8%; and
   (c) a top-coating layer comprising a portion of an active agent together with one or more excipients wherein a substantially immediate pulsed release of the active agent occurs following administration to the subject of the tablet;
   wherein the active agent in the core and on the top-coating layer is an NSAID.

2. The press-coated tablet according to claim 1 further comprising an amount of an active agent, which is the same or different to the active agent in the core and/or top-coating layer, in the delayed release layer.

3. The press-coated tablet according to claim 1 wherein the wax is selected from the group consisting of beeswax, carnuba wax, microcrystalline wax, hydrogenated castor oil, and a glyceryl ester.

4. The press-coated tablet according to claim 3 wherein the glyceryl ester is glycerol behenate.

5. The press-coated tablet according to claim 1 wherein the wax and the low substituted hydroxypropyl cellulose are present in a ratio of 45:55 to 55:45 w/w.

6. The press-coated tablet according to claim 5 wherein the wax and the low substituted hydroxypropyl cellulose are present in a ratio of 50:50 w/w ratio and wherein the wax is glycerol behenate.

7. A method of alleviating pain and/or inflammation, the method comprising administering a press-coated tablet according to claim 1.

8. The method according to claim 7 wherein the NSAID is diclofenac.

9. The method according to claim 7 wherein delayed release of the NSAID is achieved by providing a press-coated tablet comprising a delayed release layer surrounding a core comprising the NSAID agent.

10. The method according to claim 9 wherein the delayed release layer comprises a wax and a low substituted hydroxypropyl cellulose, wherein the low substituted hydroxpropyl cellulose is micronized with a mean particle diameter of 20 mm and has a molecular weight of 115,000 and a hydroxypropyl cellulose content of 8%.

11. The press-coated tablet according to claim 1, wherein the active agent is diclofenac.

12. A press-coated tablet formulation for an immediate, followed by a delayed release of an NSAID active agent, the tablet comprising:
- (a) a core comprising an active agent together with an excipient(s); and
- (b) a delayed release layer surrounding the core and comprising a wax and a low substituted hydroxypropyl cellulose in a ratio of 40:60 to 60:40 w/w; wherein the delayed release layer substantially delays release of the active agent within the core for between 3-8 hours, and thereafter a pulsed release of the active agent from the core occurs, such that at least 70% of the active agent in the core is released within 5-45 minutes; wherein the low substituted hydroxypropyl cellulose is micronized with a mean particle diameter of 20 mm and has a molecular weight of 115,000 and a hydroxypropyl cellulose content of 8%; and
- (c) a top-coating layer comprising a portion of an active agent together with one or more excipients wherein a substantially immediate pulsed release of the active agent occurs following administration to the subject of the tablet; wherein said release is measured in 900 ml of 0.01M sodium phosphate buffer at pH 7, at 37° C. as determined by UV analysis at 248 nm;

wherein the active agent in the core and on the top-coating layer is an NSAID.

13. The press-coated tablet according to claim 12 further comprising an amount of an active agent, which is the same or different to the active agent in the core and/or top-coating layer, in the delayed release layer.

* * * * *